United States Patent
Shikino

(10) Patent No.: US 9,063,236 B2
(45) Date of Patent: Jun. 23, 2015

(54) RADIATION IMAGE CAPTURING SYSTEM AND RADIATION IMAGE CAPTURING APPARATUS

(71) Applicant: Konica Minolta, Inc., Tokyo (JP)

(72) Inventor: Atsunori Shikino, Yokohama (JP)

(73) Assignee: KONICA MINOLTA, INC. (JP)

( * ) Notice: Subject to any disclaimer, the term of this patent is extended or adjusted under 35 U.S.C. 154(b) by 0 days.

(21) Appl. No.: 14/282,542

(22) Filed: May 20, 2014

(65) Prior Publication Data
US 2014/0346367 A1 Nov. 27, 2014

(30) Foreign Application Priority Data
May 27, 2013 (JP) ................................. 2013-110471

(51) Int. Cl.
| | | |
|---|---|---|
| G01J 1/42 | (2006.01) | |
| G01T 1/17 | (2006.01) | |
| H04N 5/32 | (2006.01) | |
| H04N 5/378 | (2011.01) | |
| A61B 6/00 | (2006.01) | |

(52) U.S. Cl.
CPC ................. *G01T 1/17* (2013.01); *A61B 6/4233* (2013.01); *H04N 5/32* (2013.01); *H04N 5/378* (2013.01); *A61B 6/54* (2013.01); *A61B 6/56* (2013.01)

(58) Field of Classification Search
CPC ............ G01T 1/16; G01T 1/17; G01T 1/2018
USPC .......................................................... 250/394
See application file for complete search history.

(56) References Cited

U.S. PATENT DOCUMENTS

2013/0264487 A1* 10/2013 Okada et al. .................. 250/393

FOREIGN PATENT DOCUMENTS

| JP | 6-342099 A | 12/1994 |
|---|---|---|
| JP | 9-73144 A | 3/1997 |
| JP | 2006-58124 A | 3/2006 |
| JP | 2010-104398 A | 5/2010 |
| WO | 2011/135917 A1 | 11/2011 |
| WO | 2011/152093 A1 | 12/2011 |

* cited by examiner

*Primary Examiner* — Kiho Kim
(74) *Attorney, Agent, or Firm* — Cantor Colburn LLP

(57) ABSTRACT

Disclosed are a radiation image capturing system and a radiation image capturing apparatus. According to one implementation, the radiation image capturing system includes the radiation image capturing apparatus and a console. The detecting unit of the radiation image capturing apparatus detects start of irradiation using a first detecting method in which power consumption amount is small but a capturing condition with which the start of irradiation can be detected is limited, or a second detecting method in which power consumption amount is large but the start of irradiation can be detected under any capturing condition. The console transmits a capturing condition to the radiation image capturing apparatus. The detecting unit selects the first or second detecting method based on the capturing condition, and performs processing of detecting the start of irradiation using the selected detecting method.

9 Claims, 14 Drawing Sheets

FIG.16

| CAPTURING ORDER ID | PATIENT ID | PATIENT NAME | SEX | AGE | DIAGNOSIS DEPARTMENT | CAPTURING SITE | CAPTURING DIRECTION | BUCKY ID |
|---|---|---|---|---|---|---|---|---|
| 001 | 100085 | M | MALE | 25 | ORTHOPEDIC | STOMACH PORTION | FRONT VIEW P → A | 002 |
| 002 | 100085 | M | MALE | 25 | ORTHOPEDIC | CHEST PORTION | FRONT VIEW P → A | 001 |
| 003 | 100085 | M | MALE | 25 | ORTHOPEDIC | HEAD PORTION | FRONT VIEW P → A | 001 |
| 004 | 100085 | M | MALE | 25 | ORTHOPEDIC | LEG PORTION | R | 003 |
| 005 | 100063 | W | FEMALE | 32 | SURGICAL | CHEST PORTION | SIDE VIEW R → L | 001 |
| 006 | 100063 | W | FEMALE | 32 | SURGICAL | STOMACH PORTION | FRONT VIEW A → P | 002 |

PLEASE INPUT CAPTURING ORDER INFORMATION OF PLANNED CAPTURING

| CAPTURING ORDER ID | PATIENT ID | PATIENT NAME | SEX | AGE | DIAGNOSIS DEPARTMENT | CAPTURING SITE | CAPTURING DIRECTION | BUCKY ID |
|---|---|---|---|---|---|---|---|---|
| 001 | 100085 | M | MALE | 25 | ORTHOPEDIC | STOMACH PORTION | FRONT VIEW P → A | 002 |
| 002 | 100085 | M | MALE | 25 | ORTHOPEDIC | CHEST PORTION | FRONT VIEW P → A | 001 |
| 003 | 100085 | M | MALE | 25 | ORTHOPEDIC | HEAD PORTION | FRONT VIEW P → A | 001 |
| 004 | 100085 | M | MALE | 25 | ORTHOPEDIC | LEG PORTION | R | 003 |

RETURN  ENTER

RADIATION IMAGE CAPTURING SYSTEM AND RADIATION IMAGE CAPTURING APPARATUS

CROSS REFERENCE TO RELATED APPLICATIONS

The present invention claims priority under 35 U.S.C. §119 to Japanese Application No. 2013-110471 filed May 27, 2013, the entire content of which is incorporated herein by reference.

BACKGROUND

1. Field of the Invention

The present invention relates to a radiation image capturing system and a radiation image capturing apparatus. Specifically, the present invention relates to a radiation image capturing apparatus which can detect start of irradiation of radiation and a radiation image capturing system which uses such apparatus.

2. Description of Related Art

Various radiation image capturing apparatuses are being developed. For example, there is a direct-type radiation image capturing apparatus which generates electric charge in a detecting element according to the amount of irradiated radiation such as X-ray, etc., to convert the electric charge to an electric signal. There is also an indirect-type radiation image capturing apparatus which converts the irradiated radiation to an electromagnetic wave with another wavelength such as visible light, etc., with a scintillator, etc., and then generates electric charge by a photoelectric conversion element such as photodiode, etc. according to energy of the converted and irradiated electromagnetic wave to convert the electric charge to an electric signal (in other words, image data). In the present invention, the detecting element in the direct-type radiation image capturing apparatus and the photoelectric conversion element in the indirect-type radiation image capturing apparatus are collectively referred to as a radiation detecting element.

Such type of radiation image capturing apparatus is known as an FPD (Flat Panel Detector). Conventionally, the radiation image capturing apparatuses were dedicated type apparatuses (also referred to as fixed type) formed together with a supporting stage, etc. (for example, see Japanese Patent Application Laid-Open Publication No. H9-73144). Lately, portable type (also referred to as cassette type) radiation image capturing apparatuses are developed and used where the radiation detecting element, etc., is stored in a housing so that the apparatus can be carried (for example, see Japanese Patent Application Laid-Open Publication No. 2006-058124, Japanese Patent Application Laid-Open Publication No. H6-342099).

For example, as shown in later described FIG. 3, FIG. 4, etc., in such radiation image capturing apparatuses, usually, a plurality of radiation detecting elements 7 are arranged two-dimensionally (matrix shape) on a detecting section P, and a switch element formed with a thin film transistor (hereinafter referred to as TFT) 8 is connected to each radiation detecting element 7. Usually, radiation image capturing is performed by irradiating radiation from a radiation generating apparatus 55 (see later described FIG. 5) to the radiation image capturing apparatus in a state with a predetermined capturing site (in other words, chest portion front view, lumbar spine side view, etc.) of a body, etc. of a subject in between.

Here, an off voltage is applied to each line L1 to Lx of a scanning line 5 from a gate driver 15b of a scanning driving unit 15 of the radiation image capturing apparatus to set all TFT 8 to an off state (later described electric charge accumulating state). In this state, when radiation is irradiated, electric charge is generated in each radiation detecting element 7 by irradiating the radiation, and the electric charge is accurately accumulated in each radiation detecting element 7. Then, after radiation image capturing, an on voltage is sequentially applied to each line L1 to Lx of the scanning line 5 from the gate driver 15b, and each TFT 8 is sequentially set to an on state. In this state, the electric charge generated and accumulated in each radiation detecting element 7 by irradiating radiation is sequentially discharged to each signal line 6, and each readout circuit 17 performs readout processing of image data D to read out the electric charge as image data D.

As described above, in order to accurately perform radiation image capturing, it is necessary to suitably apply off voltage to each line L1 to Lx of the scanning line 5 from the gate driver 15b to set each TFT 8 which are switch elements to the off state when the radiation is irradiated to the radiation image capturing apparatus. For example, in most conventional dedicated type radiation image capturing apparatuses, an interface is constructed with the radiation generating device. Signals are transmitted and received between each other to confirm that the radiation image capturing apparatus applied off voltage to each line L1 to Lx of the scanning line 5 and that the apparatus is set to the electric charge accumulating state. Then, the radiation is irradiated from the radiation generating apparatus.

However, for example, when the manufacturer of the radiation image capturing apparatus and the radiation generating apparatus are different, it is not always easy to construct an interface between each other, or it may not be possible to construct an interface. When an interface cannot be constructed between the radiation image capturing apparatus and the radiation generating apparatus, the radiation image capturing apparatus cannot know the timing that the radiation is irradiated from the radiation generating apparatus. Therefore, the radiation image capturing apparatus itself needs to detect that the radiation is irradiated from the radiation generating apparatus.

Lately, various radiation image capturing apparatuses are developed so that the radiation image capturing apparatus itself is able to detect the irradiation of radiation without depending on the interface between the radiation image capturing apparatus and the radiation generating apparatus. For example, Japanese Patent Application Laid-Open Publication No. 2010-104398 describes a radiation image capturing apparatus includes a radiation sensor (in other words, a sensor such as a module which is different from the radiation detecting element) and the radiation sensor detects the irradiated radiation to detect that the radiation is irradiated to the radiation image capturing apparatus. Moreover, for example, the pamphlet of WO 2011/135917 describes, before irradiating the radiation to the radiation image capturing apparatus, all TFT 8 (see later described FIG. 4, etc.) are set to an off state, the readout circuit 17 performs readout operation to perform readout processing of leak data dleak, and the apparatus itself is able to detect start of irradiation of radiation based on the read out leak data dleak. Further, for example, the pamphlet of WO 2011/152093 describes, before irradiating the radiation to the radiation image capturing apparatus, the scanning driving unit 15 and the readout circuit 17 are operated similar to the readout processing of image data D of the main image to perform readout processing of the image data, and the apparatus itself detects the start of irradiation of radiation based on the read out image data.

Below, the image data read out in the method of detecting the start of irradiation of radiation as described in the pamphlet of WO 2011/152093 is called irradiation start detecting data d, in order to distinguish such data from the image data D read out later as the main image. The method of detecting start of irradiation of radiation as described in the pamphlets of WO 2011/135917 and WO 2011/1592093 is described later (see later described detecting method 2A, 2B).

When the start of irradiation of radiation is detected based on the read out leak data dleak or the irradiation start detecting data d as described in the pamphlets of WO 2011/135917 or WO 2011/152093, as described later, there is a highly advantageous practical merit that it is possible to accurately detect start of irradiation of radiation under any capturing condition to perform capturing, for example, the radiation image capturing apparatus itself can accurately detect the start of irradiation of radiation even when weak radiation is irradiated to the radiation image capturing apparatus.

However, according to the method of detecting start of irradiation of radiation as described in the pamphlets of WO 2011/135917 and WO 2011/152093, the readout circuit 17 (see later described FIG. 4) needs to read out the leak data dleak. However, at present, the readout circuit 17 usually consumes a relatively large amount of electric power to read out data. Therefore, when such detecting methods are employed, there is a problem that the amount of electric power that is consumed becomes large when the detecting processing of start of irradiation of radiation is performed. Although such problem also occurs in a dedicated type radiation image capturing apparatus, especially when the amount of electric power that is consumed becomes large in the radiation image capturing apparatus which is a portable apparatus including a battery, the battery needs to be charged frequently and the number of radiation images which can be captured by one charge of the battery decreases. This causes problems such as reduction of efficiency in use of the radiation image capturing apparatus.

As described above, when the method of detecting start of irradiation of radiation as described in the pamphlets of WO 2011/135917 and WO 2011/152093 is employed, although it is possible to achieve the highly advantageous merit of being able to accurately detect start of irradiation of radiation under any capturing condition to perform capturing, there is a problem that the amount of electric power that is consumed becomes large.

SUMMARY

The present invention has been made in consideration of the above problems, and it is one of main objects to provide a radiation image capturing system and a radiation image capturing apparatus which can save the amount of electric power that is consumed in processing of detecting start of irradiation of radiation as much as possible while being able to accurately detect start of irradiation of radiation under any capturing condition and to accurately perform radiation image capturing.

In order to achieve at least one of the above-described objects, according to an aspect of the present invention, there is provided a radiation image capturing system and a radiation image capturing apparatus, the system including:
a radiation image capturing apparatus including,
a plurality of scanning lines and a plurality of signal lines;
a plurality of radiation detecting elements arranged two-dimensionally;
a scanning driving unit which switches voltage applied to each scanning line between on voltage and off voltage;
a switch element which is connected to each scanning line, wherein electric charge is accumulated in the radiation detecting element when the off voltage is applied, and the electric charge accumulated in the radiation detecting element is discharged to the signal line when the on voltage is applied;
a readout circuit which reads out the electric charge discharged from the radiation detecting element as image data;
a detecting unit which detects start of irradiation of radiation using either a first detecting method or a second detecting method, the first detecting method wherein consumption amount of electric power is small but a capturing condition with which the start of irradiation of radiation can be detected is limited, and the second detecting method wherein consumption amount of electric power is large but the start of irradiation of radiation can be detected under any capturing condition; and
a communication unit which communicates with an external device; and
a console including a communication unit to communicate with the radiation image capturing apparatus to be able to obtain the capturing condition,
wherein,
when the console obtains the capturing condition, the console transmits the obtained capturing condition to the radiation image capturing apparatus; and
the detecting unit of the radiation image capturing apparatus selects whether to detect the start of irradiation of radiation using either the first detecting method or the second detecting method based on the capturing condition transmitted from the console, and performs processing of detecting the start of irradiation of radiation using the selected detecting method.

BRIEF DESCRIPTION OF THE DRAWINGS

The present invention will become more fully understood from the detailed description given hereinbelow and the appended drawings, and thus are not intended to define the limits of the present invention, and wherein;

FIG. 16 is a diagram showing an example of capturing order information; and

FIG. 17 is a diagram showing an example of a selection screen which displays capturing order information.

DETAILED DESCRIPTION OF PREFERRED EMBODIMENTS

Below, an embodiment of the radiation image capturing system and the radiation image capturing apparatus of the present invention is described with reference to the drawings.

Below, as the radiation image capturing apparatus, an indirect type radiation image capturing apparatus is described. Such radiation image capturing apparatus includes a scintillator, etc., and converts the radiated radiation to an electromagnetic wave with another wavelength such as a visible ray, etc., to obtain an electric signal. However, the present invention can be applied to a direct type radiation image capturing apparatus which directly detects the radiation with a radiation detecting element without using a scintillator, etc. Here, a portable radiation image capturing apparatus is described. However, the present invention can be applied to a dedicated type radiation image capturing apparatus formed together with a supporting stage, etc.

[Radiation Image Capturing Apparatus]

Figure 1:
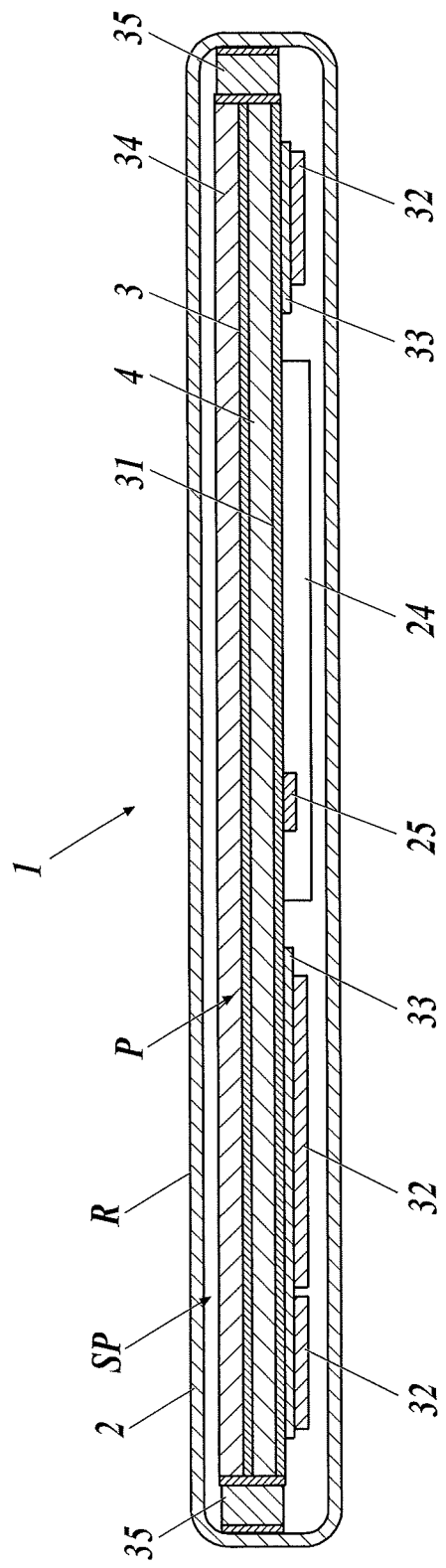
FIG. 1 is a cross-sectional view of a radiation image capturing apparatus.

First, a configuration of a radiation image capturing apparatus used in a radiation image capturing system of the present embodiment is described. FIG. 1 is a cross-sectional view of the radiation image capturing apparatus of the present embodiment. Below, a radiation image capturing apparatus 1 is described based on a vertical direction and horizontal direction in a state where the radiation image capturing apparatus 1 is placed on a horizontal plane so that a radiation entrance face R which is a face where radiation is irradiated is on an upper side as shown in FIG. 1. The relative size, length, etc. of each member of the radiation image capturing apparatus 1 in each diagram does not always reflect the actual configuration of the radiation image capturing apparatus.

As shown in FIG. 1, the radiation image capturing apparatus 1 is composed of a case 2 formed with a carbon plate, etc. including the radiation entrance face R, and stored inside the case 2 is a sensor panel SP including a scintillator 3, a substrate 4, and the like. Although not shown in FIG. 1, according to the present embodiment, case 2 is provided with an antenna apparatus 41 (see later described FIG. 4) which is a wireless communication unit for transmitting image data D, etc. in a wireless method to a later described console 58 (see later described FIG. 5 and FIG. 6). Although not shown in FIG. 1, according to the present embodiment, the radiation image capturing apparatus 1 includes a connector 42 (see later described FIG. 4) on a side face, etc. of the case 2, and signals, data, etc. can be transmitted in a wired method to the console 58, etc., through the connector 42. As shown in later described FIG. 4, the antenna apparatus 41, the connector 42 and the like are connected to a communication unit 40, and the communication unit 40 functions as a communication unit of the radiation image capturing apparatus 1.

As shown in FIG. 1, a base 31 is provided in the case 2, and a substrate 4 is provided on a radiation entrance face R side, in other words an upper face side of the base 31, with a thin lead plate, etc. (not shown) in between. A scintillator 3 which converts the irradiated radiation to light such as visible light is provided on a scintillator substrate 34 on an upper face side of the substrate 4, and the scintillator 3 is provided opposed to the substrate 4 side. A PCB substrate 33 provided with electronic components 32, etc., a battery 24, and the like are attached on a lower face side of the base 31. A radiation sensor 25 is also attached on the lower face side of the base 31. According to the present embodiment, as shown in FIG. 2, the radiation sensor 25 is provided in a center position on a lower face side of the base 31, however, the attachment position does not have to be a center position.

Figure 2:
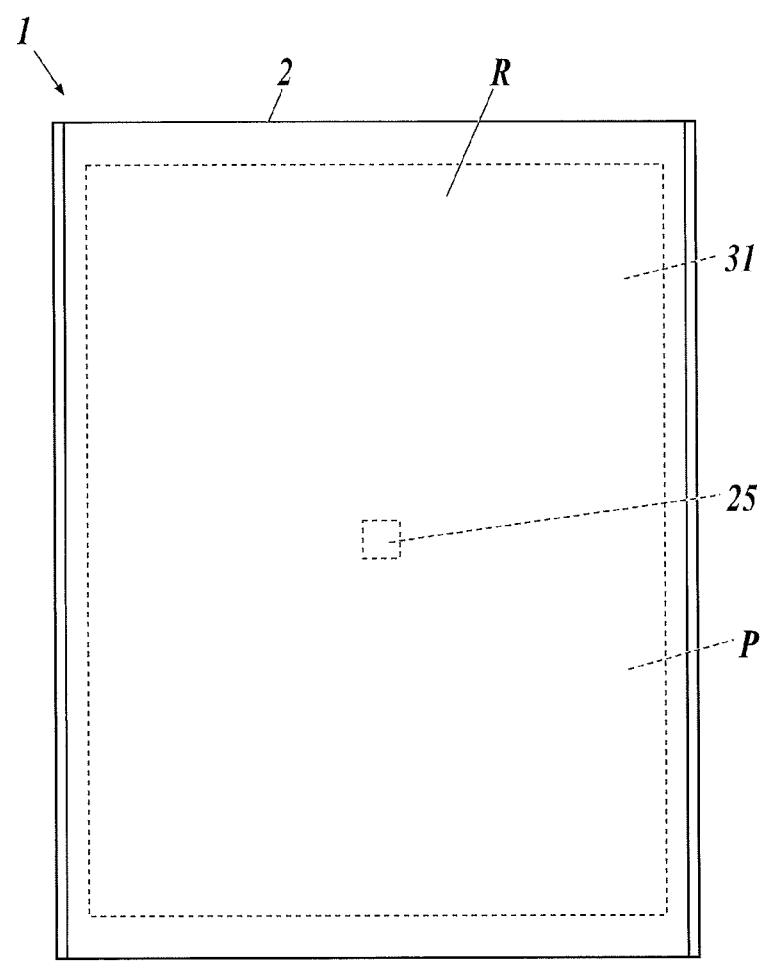
FIG. 2 is a diagram of the radiation image capturing apparatus as shown in FIG. 1 viewed from above.

FIG. 2 is a diagram of the radiation image capturing apparatus 1 viewed from the radiation entrance face R side, in other words, the upper side. FIG. 2 shows the radiation sensor 25 directly attached to the base 31. Alternatively, the radiation sensor 25 can be attached to the base 31 through the PCB substrate 33, etc., or the radiation sensor 25 can be attached on the inner side of the case 2, and the radiation sensor 25 can be attached to the radiation image capturing apparatus 1 with a suitable method at a suitable position. Instead of providing only one radiation sensor 25 as described in the present embodiment, a plurality of radiation sensors 25 can be provided. In this case, the radiation sensor 25 can be provided in a suitable position such as an edge portion of the radiation entrance face R of the radiation image capturing apparatus 1.

According to the present embodiment, the sensor panel SP is formed with the base 31, substrate 4, and the like as described above. In the present embodiment, buffer material 35 is provided between the sensor panel SP and the side face of the case 2.

Figure 3:
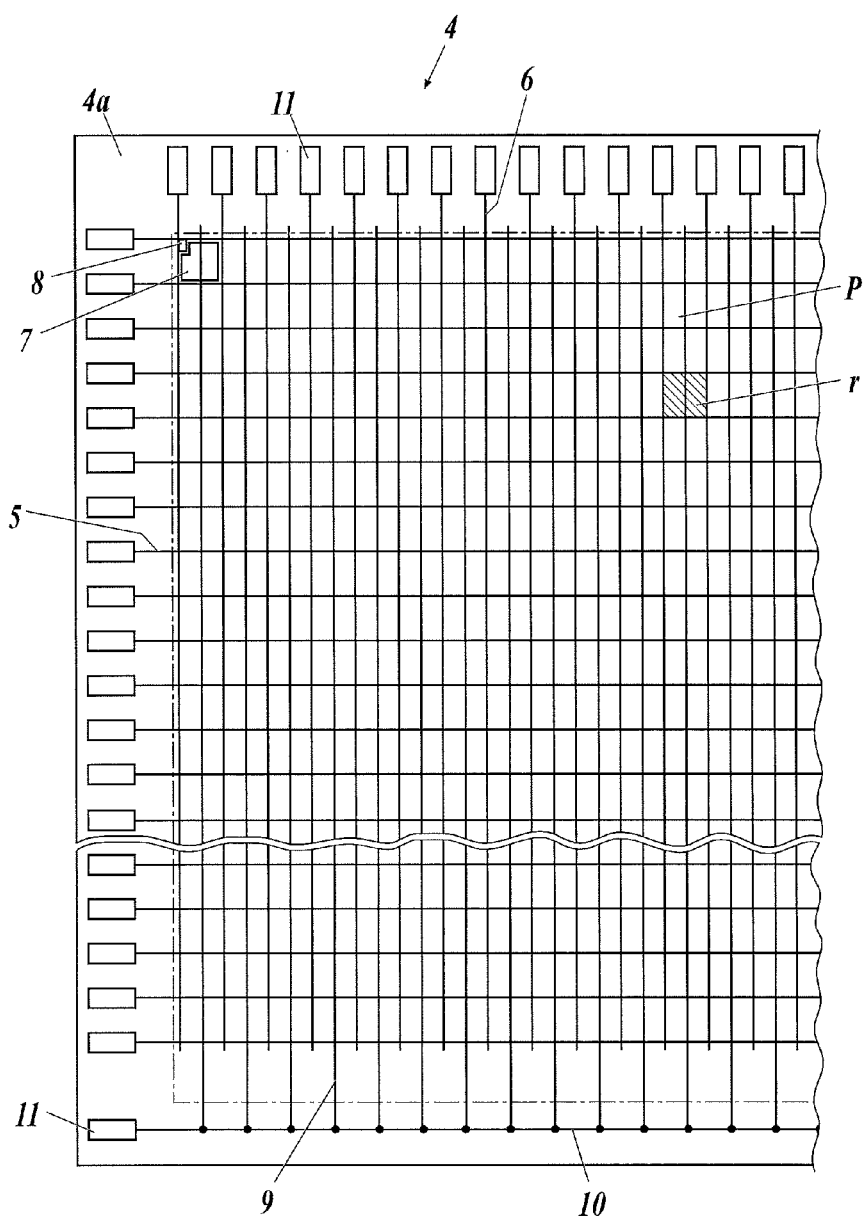
FIG. 3 is a planar view showing a configuration of a substrate of the radiation image capturing apparatus.

According to the present embodiment, the substrate 4 is composed of a glass substrate, and as shown in FIG. 3, a plurality of scanning lines 5 and a plurality of signal lines 6 are provided so as to cross each other on an upper face 4a (in other words, the face opposing to the scintillator 3) of the substrate 4. A radiation detecting element 7 is provided in each small region r divided by a plurality of scanning lines 5 and a plurality of signal lines 6 on the face 4a of the substrate 4. The entire region where the plurality of radiation detecting elements 7 are arranged two-dimensionally (matrix shape), in other words, the region shown with alternate short and long dash line in FIG. 3 is to be the detecting section P. According to the present embodiment, a photodiode is used in the radiation detecting element 7. However, for example, a phototransistor or the like can be used.

Figure 4:
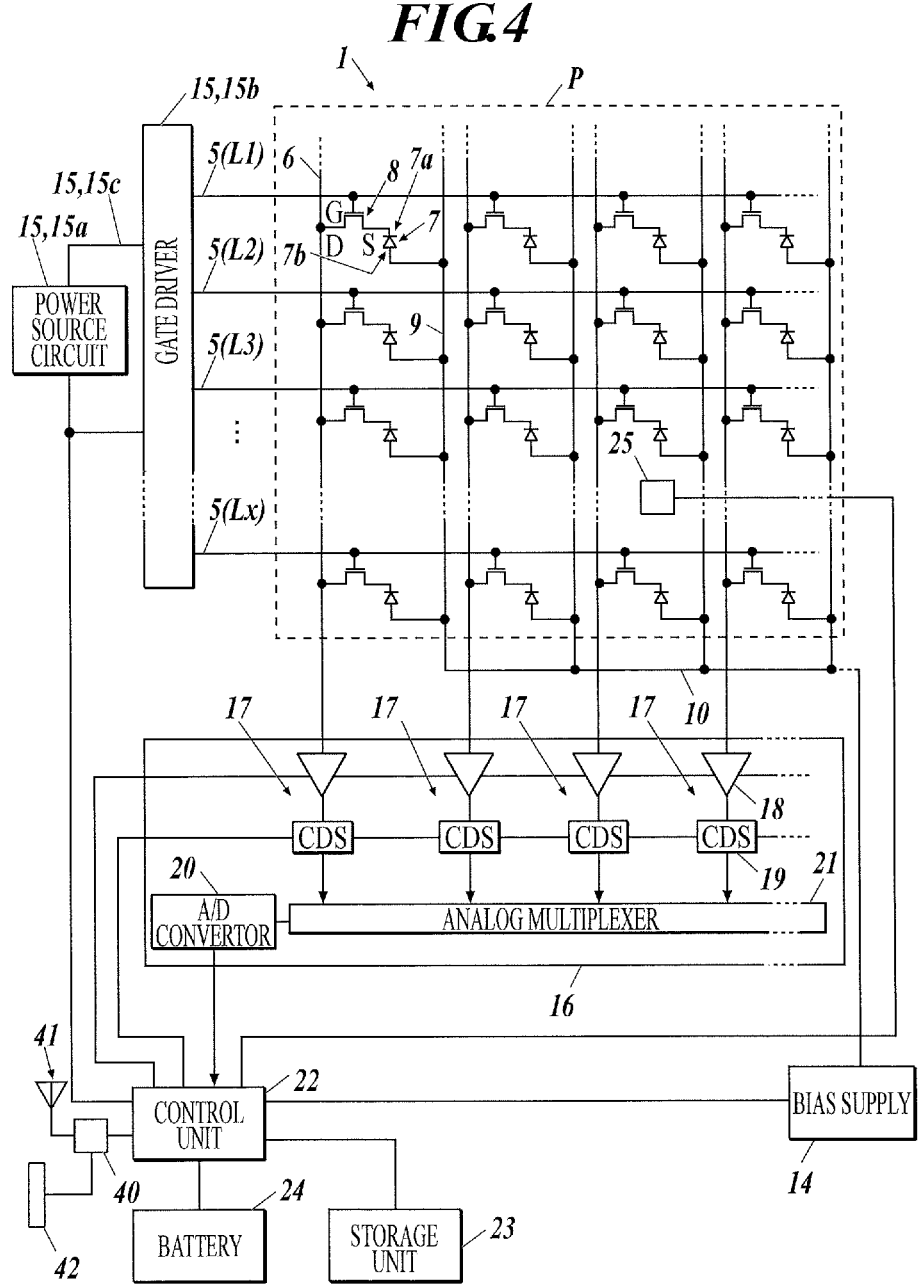
FIG. 4 is a block diagram showing an equivalent circuit of the radiation image capturing apparatus.

Here, the circuit configuration of the radiation image capturing apparatus 1 is described. FIG. 4 is a block diagram showing an equivalent circuit of the radiation image capturing apparatus 1 of the present embodiment. A source electrode 8s (see "S" in FIG. 4) of the TFT 8 which is the switch element is connected to a first electrode 7a of each radiation detecting element 7. A drain electrode 8d and a gate electrode 8g (see "D" and "G" in FIG. 4) of the TFT 8 are respectively connected to the signal line 6 and the scanning line 5. When on voltage is applied to the gate electrode 8g through the scanning line 5 from the later described scanning driving unit 15, the TFT 8 is set to an on state and discharges electric charge accumulated in the radiation detecting element 7 through the source electrode 8s and the drain electrode 8d to the signal line 6. When off voltage is applied to the gate electrode 8g through the scanning line 5, the TFT 8 is set to an off state, and the discharge of electric charge to the signal line 6 from the radiation detecting element 7 is stopped to accumulate electric charge in the radiation detecting element 7.

As shown in FIG. 3 and FIG. 4, according to the present embodiment, one bias line 9 is provided for each column of radiation detecting element 7 on the substrate 4, and the bias line 9 is connected to a second electrode 7b of each radiation detecting element 7. Each bias line 9 is connected to a connecting line 10 in a position outside the detecting section P of the substrate 4. The connecting line 10 is connected to a bias supply 14 (see FIG. 4) through an input/output terminal 11 (also referred to as a pad, see FIG. 3), and a reverse bias voltage is applied from the bias supply 14 through the connecting line 10 and bias lines 9 to the second electrode 7b of each radiation detecting element 7.

Each scanning line 5 is connected to a gate driver 15b of the scanning driving unit 15 through the input/output terminal 11. In the scanning driving unit 15, on voltage and off voltage are supplied from a power source circuit 15a through a line 15c to the gate driver 15b. The gate driver 15b switches the voltage applied to each line L1 to Lx of the scanning line 5 between on voltage and off voltage. Each signal line 6 is connected to each readout circuit 17 included in a readout IC 16 through the input/output terminal 11. According to the present embodiment, the readout circuit 17 is mainly composed of an amplifying circuit 18 and a correlated double sampling circuit 19. According to the present embodiment, as shown in later described FIG. 7, the amplifying circuit 18 is composed of a charge amplifying circuit in which an operational amplifier 18a and a capacitor 18b are connected parallel, and a voltage value according to the amount of electric charge accumulated in the capacitor 18b is output from the output side of the operational amplifier 18a. As shown in FIG. 4, an analog multiplexor 21 and an A/D convertor 20 are provided in the readout IC 16. In FIG. 4, the correlated double sampling circuit 19 is denoted by CDS.

In readout processing of image data D from each radiation detecting element 7, when on voltage is applied to a scanning line 5 from the gate driver 15b of the scanning driving unit 15 and each TFT 8 is set to an on state, electric charge is discharged through each TFT 8 from each radiation detecting element 7 to the signal line 6. Then, as described above, in the amplifying circuit 18 of each readout circuit 17, the voltage value according to the amount of electric charge which flows from the radiation detecting element 7 to the capacitor 18b is output from the operational amplifier 18a to the correlated double sampling circuit 19. The correlated double sampling circuit 19 outputs increase amount of the output value from the amplifying circuit 18 from before the electric charge is flown from each radiation detecting element 7 to the amplifying circuit 18 to after the electric charge is flown as image data D in an analog value to the downstream side. Then, each piece of output image data D is sequentially transmitted through the analog multiplexer 21 to the A/D converter 20. The A/D converter 20 sequentially converts the image data D in an analog value to image data D in a digital value and the image data D is output to the storage unit 23 to be sequentially stored. With this, the readout processing of the image data D is performed.

In the reset processing of each radiation detecting element 7, on voltage is sequentially applied to each line L1 to Lx of the scanning line 5 from the gate driver 15b (for example, see "R" in FIG. 9), the electric charge is discharged from each radiation detecting element 7 through the TFT 8 to the signal line 6, and the electric charge is flown to the downstream side. With this, the electric charge remaining in each radiation detecting element 7 is removed from each radiation detecting element 7, and each radiation detecting element 7 is reset.

The control unit 22 includes a computer in which a CPU (Central Processing Unit), a ROM (Read Only Memory), a RAM (Random Access Memory), an input/output interface, etc. (all not shown) are connected by a bus, a FPGA (Field Programmable Gate Array) and the like. The control unit 22 can be a dedicated control circuit. The control unit 22 controls the operation of each functional unit of the radiation image capturing apparatus 1, such as controlling the scanning driving unit 15 and the readout circuit 17 to perform readout processing of image data D as described above. As shown in FIG. 4, a storage unit 23 composed of a SRAM (Static RAM), SDRAM (Synchronous DRAM), etc. is connected to the control unit 22. According to the present embodiment, a communication unit 40 to which the above described antenna apparatus 41, connector 42, etc. are connected is connected to the control unit 22. Further, a battery 24 which supplies necessary electric power to each functional unit such as the scanning driving unit 15, the readout circuit 17, the storage unit 23, the bias supply 14, etc., is connected to the control unit 22.

In the present embodiment, the control unit 22 functions as a later described detecting unit of the radiation image capturing apparatus 1. However, the detecting unit can be provided as a unit different from the control unit 22. In the description below, the control unit 22 is described as the detecting unit 22 when the control unit 22 functions as the detecting unit 22. The above described radiation sensor 25 is electrically connected to the detecting unit 22, and the signal output from the radiation sensor 25 is input to the detecting unit 22. The processing performed in the radiation image capturing apparatus 1 in radiation image capturing is described after describing the configuration of the radiation image capturing system 50 of the present embodiment.

[Radiation Image Capturing System]

Figure 5:
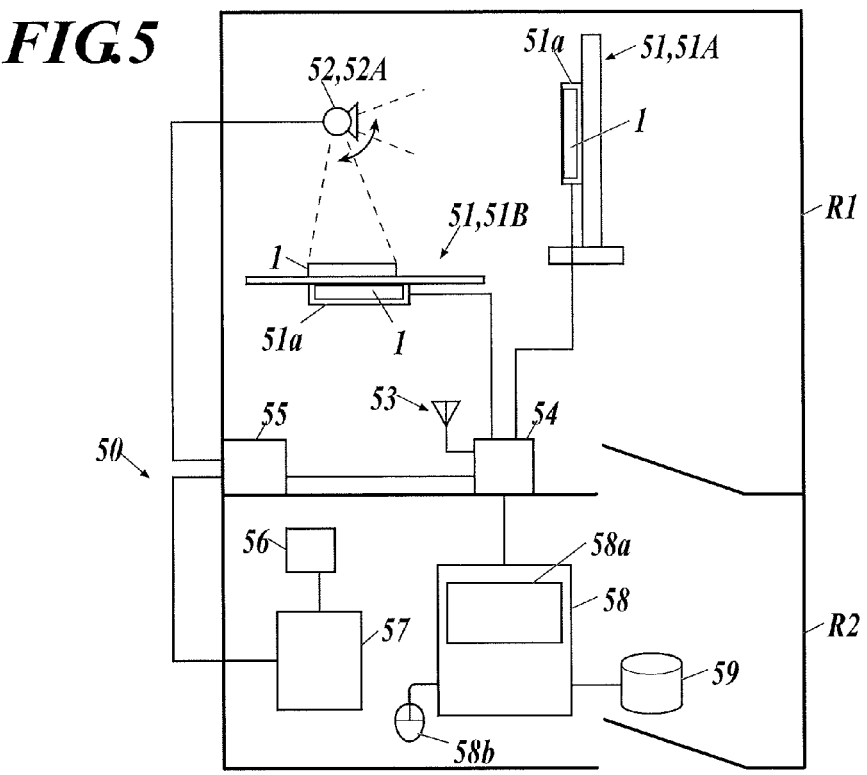
FIG. 5 is a diagram showing an example of a configuration of a radiation image capturing system of the present embodiment constructed in a capturing room, etc.

Next, the configuration of the radiation image capturing system 50 of the present embodiment is described. FIG. 5 is a diagram showing an example of a configuration of the radiation image capturing system 50 of the present embodiment. FIG. 5 shows a radiation image capturing system 50 constructed in a capturing room R1, etc.

A bucky apparatus 51 is provided in the capturing room R1, and the bucky apparatus 51 can be used by attaching the radiation image capturing apparatus 1 to the cassette holding unit 51a (also referred to as a cassette holder). FIG. 5 shows a standing position capturing bucky apparatus 51A and a recumbent position capturing bucky apparatus 51B are provided as the bucky apparatus 51. Alternatively, for example, only one of the above bucky apparatus can be provided. As shown in FIG. 5, at least one radiation source 52A of a radiation generating apparatus 55 which irradiates radiation to the radiation image capturing apparatus 1 including the bucky apparatus 51 with the subject in between is provided in the capturing room R1. According to the present embodiment, radiation can be irradiated to either of the standing position capturing bucky apparatus 51A or the recumbent position capturing bucky apparatus 51B by moving the position of the radiation source 52A or changing the irradiating direction of radiation.

A relay 54 (also referred to as a base station, etc.) to relay communication among apparatuses inside and outside the capturing room R1 is provided in the capturing room R1. According to the present embodiment, an access point 53 is provided in the relay 54 so that the radiation image capturing apparatus 1 is able to transmit and receive image data D, signals, etc. with a wireless method. The relay 54 includes a converter (not shown) which converts a signal for LAN communication transmitted from the radiation image capturing apparatus 1, console 58, etc., to the radiation generating apparatus 55, to a signal for the radiation generating apparatus 55, and vice versa. According to the present embodiment, the relay 54 functions as a communication unit of the console 58 side for communication between the console 58 and other apparatuses.

According to the present embodiment, an operating desk 57 of the radiation generating apparatus 55 is provided in a front room (also referred to as an operation room) R2. An exposure switch 56 which is operated by an operator such as a radiation technologist to instruct start of irradiation of radiation to the radiation generating apparatus 55 is provided in the operating desk 57. When the operator operates the exposure switch 56, the radiation generating apparatus 55 irradiates radiation from the radiation source 52. Based on capturing conditions, such as tube voltage set in the console 58, etc., the radiation generating apparatus 55 performs various control such as adjust the radiation source 52 by providing the set tube voltage to the radiation source 52 so that radiation in a suitable amount and rate (in other words, amount of radiation for each unit of time) is irradiated from the radiation source 52.

As shown in FIG. 5, according to the present embodiment, a console 58 including a computer, etc., is provided in the front room R2. The console 58 can be provided outside the capturing room R1 or the front room R2, or can be provided in a separate room, and the console 58 is provided in a suitable place. The console 58 is provided with a display unit 58a including a CRT (Cathode Ray Tube), LCD (Liquid Crystal Display), etc., and includes an input unit 58b such as a mouse or a keyboard. A storage unit 59 including an HDD (Hard Disk Drive), etc. is connected to or included in the console 58.

Figure 6:
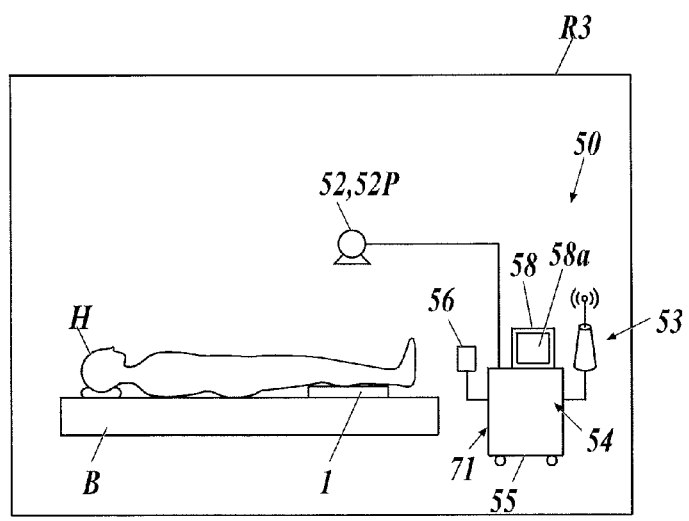
FIG. 6 is a diagram showing an example of a configuration of a radiation image capturing system of the present embodiment constructed on a car for medical rounds.

As shown in FIG. 6, the radiation image capturing apparatus 1 can be used in an independent state without attaching to the bucky apparatus 51. For example, when a patient H in a patient room R3 cannot get up from a bed B and therefore cannot go to the capturing room R1, or when radiation image capturing is performed by bringing the radiation image capturing system 50 including the radiation image capturing apparatus 1 to a home care patient's home, as shown in FIG. 6 illustrating the patient room R3, the radiation image capturing apparatus 1 can be brought into the patient room R3 and the radiation image capturing apparatus 1 can be used by placing the radiation image capturing apparatus 1 between the bed B and the body of the patient or placing the radiation image capturing apparatus 1 against the body of the patient.

When the radiation image capturing apparatus 1 is used in a patient room R3, etc., instead of the above described radiation generating apparatus 55 provided fixed to the capturing room R1, as shown in FIG. 6, a portable radiation generating apparatus 55 is brought in the patient room R3 by for example, mounting the portable radiation generating apparatus 55 on a car 71 for making rounds. The illustrations of the input unit 58b of the console 58, the storage unit 59, and the like are omitted in FIG. 6. Here, the radiation source 52P of the portable radiation generating apparatus 55 is configured to be able to irradiate radiation in any direction, and the radiation can be irradiated from a suitable distance or direction to the radiation image capturing apparatus 1 placed between the bed B and the body of the patient or placed against the body of the patient. In this case, the relay 54 provided with an access point 53 is included in the radiation generating apparatus 55, and as described above, the relay 54 relays communication between the radiation generating apparatus 55 and the console 58, and communication and transmission of image data D between the radiation image capturing apparatus 1 and the console 58.

As shown in FIG. 5, the radiation image capturing apparatus 1 can be placed between the recumbent position capturing bucky apparatus 51B and the body of the patient (not shown) lying on the recumbent position capturing bucky apparatus 51B of the capturing room R1, or the radiation image capturing apparatus 1 can be placed against the body of the patient on the recumbent position capturing bucky apparatus 51B. In this case, either the portable radiation generating apparatus 55 or the radiation generating apparatus 55 provided fixed to the capturing room R1 can be used. According to the present embodiment, the console 58 can transmit a signal, etc., to the radiation image capturing apparatus 1 and the radiation generating apparatus 55 to control the above. Alternatively, when the image data D, etc., is transmitted from the radiation image capturing apparatus 1, the console 58 functions as an image processing apparatus which performs fine image processing such as gain correction, defective pixel correction, gradation processing according to the capturing site, etc., based on the above data and generates the radiation image.

[Detecting Processing of Start of Irradiation of Radiation in Radiation Image Capturing Apparatus]

Described here is detecting processing of start of irradiation of radiation performed by the radiation image capturing apparatus 1 used in the radiation image capturing system 50 of the present embodiment. According to the present embodiment, the detecting unit 22 (in other words, the control unit 22 of the present embodiment) of the radiation image capturing apparatus 1 is able to detect the start of irradiation of radiation from the radiation generating apparatus 55 by at least two detecting methods, and as described later, the detecting unit 22 selects either one of the detecting methods based on the capturing condition to detect the start of irradiation of radiation.

[First Detecting Method]

According to the present embodiment, as the first detecting method, the detecting unit 22 of the radiation image capturing apparatus 1 is able to detect the start of irradiation of radiation based on the value output from the radiation sensor 25 described above (see FIG. 1, FIG. 2, and FIG. 4). Specifically, for example, a semiconductor sensor, etc. in which the output electric current value or voltage value becomes large when the radiation is irradiated can be used as the radiation sensor 25. For example, a threshold value for value output from the radiation sensor 25 can be set in advance, and it is possible to set the detecting unit 22 to detect start of irradiation of radiation when the value output from the radiation sensor 25 becomes a value equal to or more than the threshold value. The on voltage is sequentially applied to each line L1 to Lx of the scanning line 5 from the gate driver 15b (see FIG. 4) to perform reset processing of each radiation detecting element 7 while the detecting unit 22 of the radiation image capturing apparatus 1 performs processing to detect start of irradiation of radiation using the first detecting method so that dark electric charge is not accumulated in each radiation detecting element 7.

[Second Detecting Method]

According to the present embodiment, as the second detecting method, the detecting unit 22 of the radiation image capturing apparatus 1 is able to detect the start of the irradiation of radiation using the detecting method as described in the pamphlets of above noted WO 2011/135917 and WO 2011/152093. The detecting method as described in the pamphlets of above noted WO 2011/135917 and WO 2011/152093 and the detecting method further modifying the above are described below.

[Detecting Method 2A]

It is possible to apply off voltage to each scanning line 5 from the gate driver 15b (see FIG. 4) from before irradiating the radiation to the radiation image capturing apparatus 1, and each readout circuit 17 is able to perform readout in a state where each TFT 8 is in an off state to repeat the readout processing of the leak data dleak. The detecting processing 2A is discussed in detail in the pamphlet of WO 2011/135917.

Figure 7:
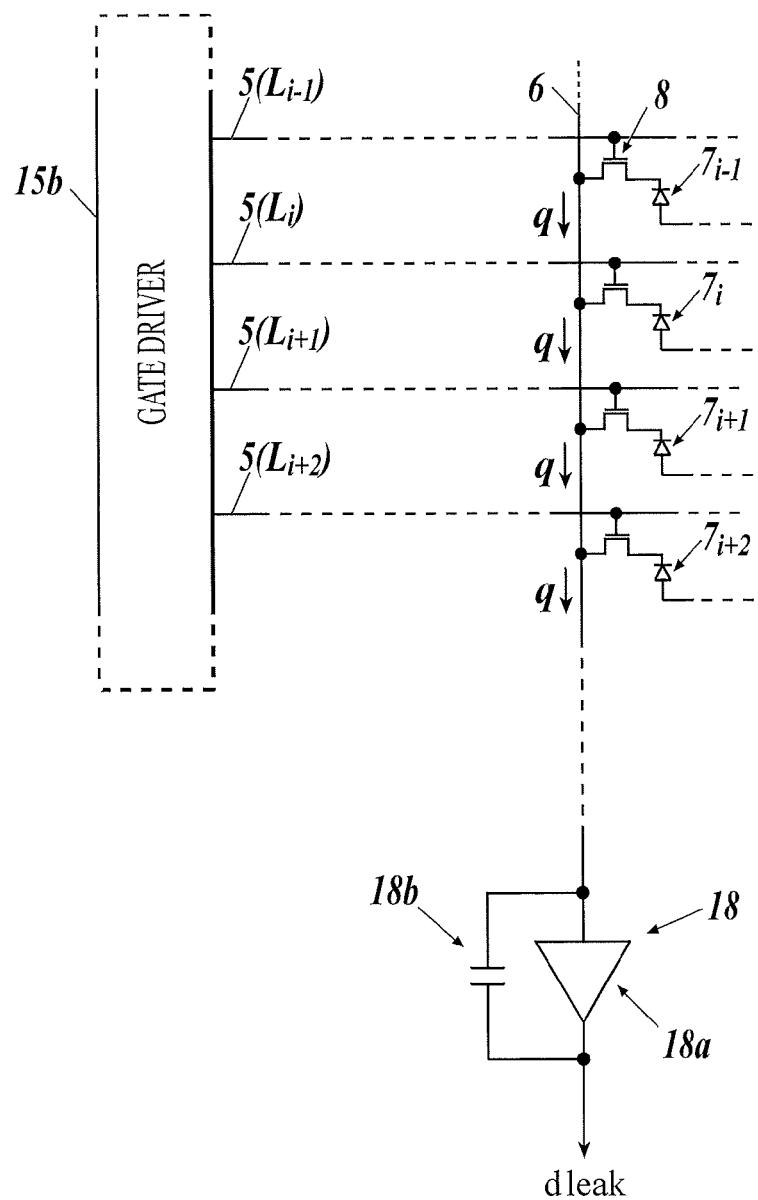
FIG. 7 is a diagram describing electric charge which leaked from each radiation detecting element through each TFT read out as leak data.

As shown in FIG. 7, when the off voltage is applied to each scanning line 5 from the gate driver 15b to set each TFT 8 to the off state, the electric charge q which leaks from each radiation detecting element 7 through each TFT 8 in the off state is accumulated in the capacitor 18b of the amplifying circuit 18. In other words, the total value of the electric charge q which leaks from each radiation detecting element 7 through each TFT 8 is accumulated in the capacitor 18b of the amplifying circuit 18. Therefore, when the readout circuit 17 performs readout in this state, the voltage value according to the total value of electric charge q which leaks from each radiation detecting element 7 through each TFT 8 is output from the output side of the operational amplifier 18a of the amplifying circuit 18. Therefore, the data corresponding to the total value of the electric charge q which leaks through each TFT 8 is read out. The data read out as described above is leak data dleak. Then, in this configuration also, when the irradiation of radiation to the radiation image capturing apparatus 1 starts, the electric charge q which leaks to the signal line 6 from each radiation detecting element 7 through each TFT 8 increases. Therefore, it is known that the value of the read out leak data dleak drastically increases when the irradiation of radiation to the radiation image capturing apparatus 1 starts (for example, see time t1 of FIG. 8).

Figure 8:
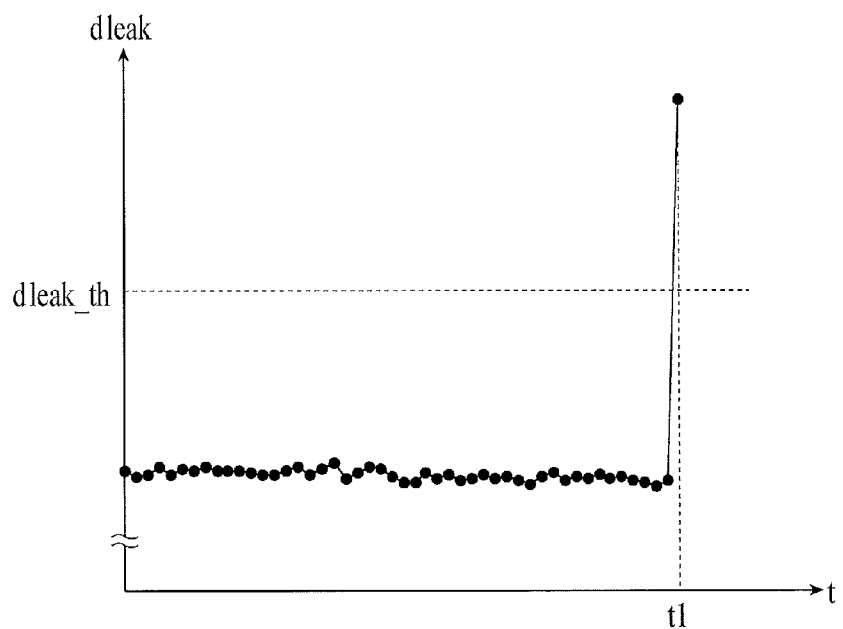
FIG. 8 is a graph showing an example of development through time of read out leak data.

The value of the leak data dleak increasing is used to detect the start of irradiation of radiation with the radiation image capturing apparatus 1 itself by detecting that the read out leak data dleak is equal to or larger than the set threshold value dleak_th as shown in FIG. 8.

Figure 9:
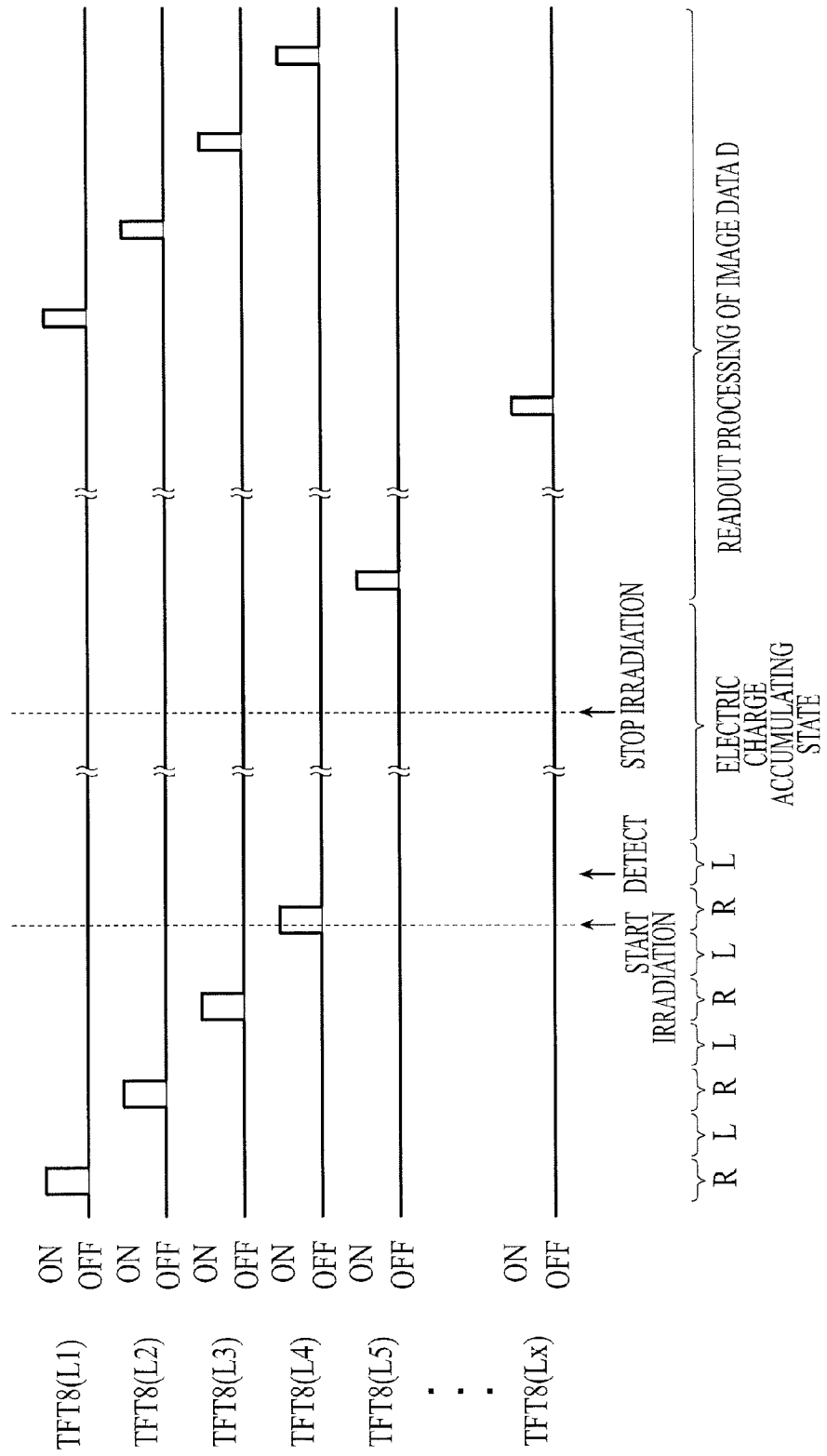
FIG. 9 is a timing chart describing timing, etc. of applying on voltage to each scanning line when start of irradiation of radiation is detected based on the leak data.

When the start of irradiation of radiation is detected using the leak data dleak, if the off voltage is applied to each scanning line 5 from the gate driver 15b and each TFT 8 is left in the off state, the dark electric charge continues to be accumulated in each radiation detecting element 7. Therefore, for example, as shown in the left side portion of FIG. 9 described below, it is possible to configure the apparatus to perform reset processing of each radiation detecting element 7 (described as "R" in the diagram) between readout processing of the leak data dleak (described as "L" in the diagram) and the readout processing of the next leak data dleak. When the reset processing of each radiation detecting element 7 is performed, as shown in FIG. 9, the on voltage can be sequentially applied to each line L1 to Lx of the scanning line 5 from the gate driver 15b of the scanning driving unit 15 (see FIG. 4), or although not shown, on voltage can be applied to lines L1 to Lx of the scanning line 5 at once from the gate driver 15b.

[Detecting Method 2B]

Alternatively, instead of performing the readout processing of leak data dleak from before the radiation is irradiated to the radiation image capturing apparatus 1, it is possible to drive the scanning driving unit 15 and each readout circuit 17 (see FIG. 4) to repeat the above described readout processing of the irradiation start detecting data d. The detecting method 2B is described in detail in the pamphlet of WO 2011/152093.

When the apparatus is configured as described above, before the irradiation of radiation to the radiation image capturing apparatus 1 starts, since the radiation is not yet irradiated to the radiation image capturing apparatus 1, the data due to the dark electric charge generated in each radiation detecting element 7 is read out as the irradiation start detecting data d. When the irradiation of radiation to the radiation image capturing apparatus 1 starts, the electric charge is generated in each radiation detecting element 7 by the irradiation of radiation, and this is read out as the irradiation start detecting data d. Therefore, similar to the above described leak data dleak (see FIG. 8), the value of the read out irradiation start detecting data d drastically increases when the irradiation of radiation to the radiation image capturing apparatus 1 starts.

Therefore, in the detecting method 2B also, it is possible to detect the start of irradiation of radiation with the radiation image capturing apparatus 1 itself by, for example, detecting that the read out irradiation start detecting data d is equal to or larger than the set threshold value dth.

[Processing after Detecting Start of Irradiation of Radiation]

In both the first detecting method and the second detecting method (in other words, detecting method 2A and detecting method 2B), as shown in FIG. 9 describing detecting method 2A, when the control unit 22 of the radiation image capturing apparatus 1 detects the start of irradiation of radiation to the radiation image capturing apparatus 1 (see "detect" in the diagram), the off voltage is applied to each line L1 to Lx of the scanning line 5 from the gate driver 15b. Then, the processing advances to the electric charge accumulating state where all of the TFT 8 are set to the off state, and the electric charge generated in each radiation detecting element 7 by the irradiation of radiation is accumulated in each radiation detecting element 7. Then, for example, after a predetermined amount of time passes after advancing to the electric charge accumulating state, the readout processing of the image data D as the main image starts.

According to the present embodiment, as shown in FIG. 9, in the readout processing of image data D, the on voltage is applied starting from the scanning line 5 to be applied with the on voltage next (line L5 of scanning line 5 in FIG. 9) after the scanning line 5 applied with the on voltage when the start of irradiation of radiation is detected or directly before the start is detected (line L4 of scanning line 5 in FIG. 9), and the on voltage is sequentially applied to each scanning line 5 from the gate driver 15b to perform readout processing of the image data D as the main image. However, the readout processing of the image data D is not limited to the above, and although not shown, for example, it is possible to perform the readout processing of the image data D as the main image by applying the on voltage starting from the first line L1 of the scanning line 5 and sequentially applying the on voltage to each line L1 to Lx of the scanning line 5.

Then, the read out image data D, etc., is transmitted from the above described communication unit 40 (see FIG. 4) through the antenna apparatus 41, connector 42, etc., by the wireless or wired method to the console 58 (see FIG. 5 and FIG. 6), and as described above, the console 58 performs generating processing, etc. of the radiation image based on the transmitted image data D, etc.

[Detecting Method of Start of Irradiation of Radiation Modified from Second Detecting Method]

The detecting method 2A and the detecting method 2B of the above described second detecting method can be modified as described below. Below, mainly the detecting method 2A is described, in other words, the method of detecting the start of irradiation of radiation based on the leak data dleak read out by alternately performing the readout processing of leak data dleak before radiation image capturing and the reset processing of each radiation detecting element 7. However, the description below also applies when the detecting method 2B is employed. The details of the modified detecting method is described in Japanese Patent Application Laid-Open Publication No. 2012-176155.

[Detecting Method 2α (Difference Method)]

For example, in one readout processing of leak data dleak, an average value, a total value, an intermediate value, a maximum value, etc. (hereinafter collectively referred to as statistic value dleak_st(z) (z is the number of readout IC 16)) of the 128 pieces or 256 pieces of leak data dleak output from each of the 128 or 256 readout circuits 17 in one readout IC 16 is calculated. The maximum value can be extracted from the statistic value dleak_st(z) and it is possible to judge whether the maximum value of the statistic value dleak_st(z) of the leak data dleak is equal to or more than a threshold value. According to such configuration, instead of judging whether the value of all pieces of leak data dleak read out in one readout processing is equal to or more than the threshold dleak_th, it is only necessary to judge whether the one maximum value extracted from the statistic value dleak_st(z) is equal to or more than the threshold value, and the detecting processing becomes very light.

Figure 10:
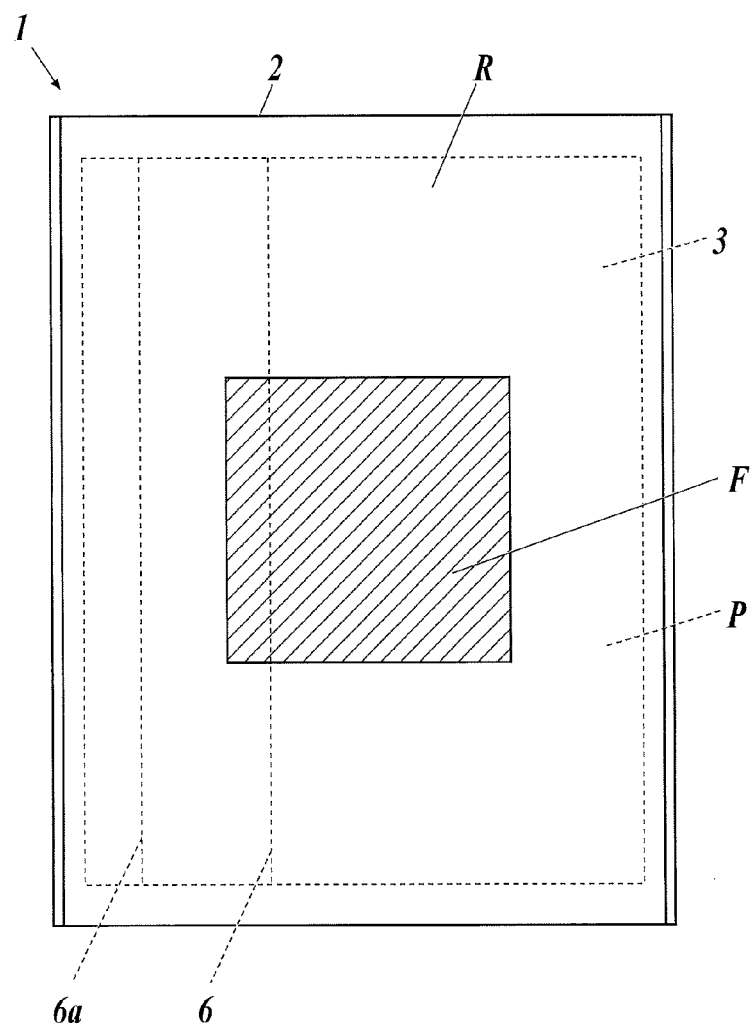
FIG. 10 is a diagram showing when radiation is irradiated to the radiation image capturing apparatus with the irradiating field of the radiation narrowed.
Figure 11:
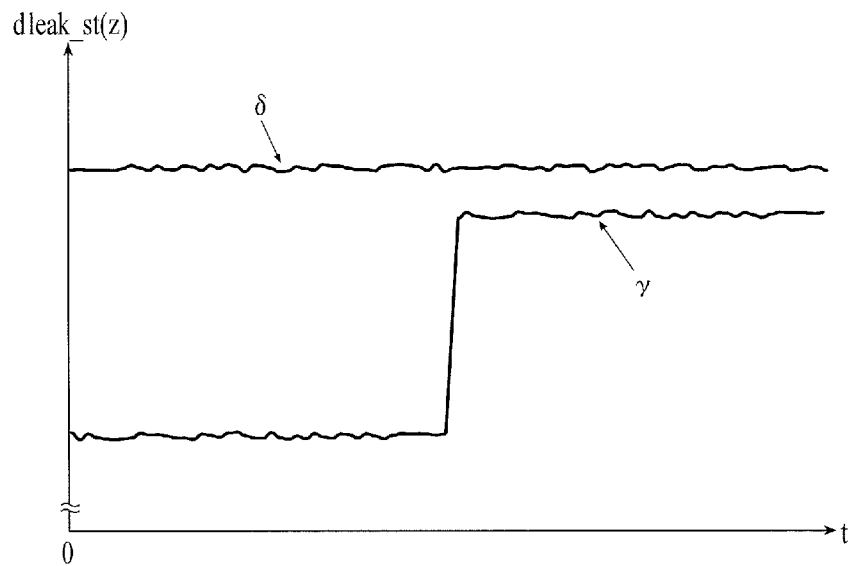
FIG. 11 is a graph showing an example of development through time of an average value for each readout IC of leak data read out by each readout circuit.

However, even if the total value of the electric charge q (see FIG. 7) which leaks from each radiation detecting element 7 to the signal line 6 is the same for each signal line 6, there is a readout IC 16 where the statistic value dleak_st(z) of the leak data dleak becomes constantly larger or smaller than the other readout IC 16, depending on the readout attribute of each readout IC 16. For example, as shown in FIG. 10, when the radiation to the radiation image capturing apparatus 1 is irradiated so that the irradiating field F is narrowed to the center portion of the detecting section P and there is a signal line 6*a* outside of the irradiating field F connected to a readout IC 16 in which the statistic value dleak_st(z) of the leak data dleak becomes constantly larger than the other readout IC 16, as shown in FIG. 11, even if the statistic value dleak_st(z) (see γ in diagram) of the leak data dleak output from the readout IC 16γ connected to the signal line 6 inside the irradiating field F rises due to the irradiation of radiation, the value may not become equal to or larger than the statistic value dleak_st(z) (see δ in diagram) of the leak data dleak output from the readout IC 16δ connected to the signal line 6 outside the irradiating field F. When the maximum value is extracted from the statistic values dleak_st(z) in this state, the statistic value dleak_st(z) of the leak data dleak shown with a δ in the diagram is extracted, but the extracted statistic value dleak_st(z) of the leak data dleak does not change by the irradiation of radiation. As a result, the irradiation of radiation cannot be detected.

Figure 12:
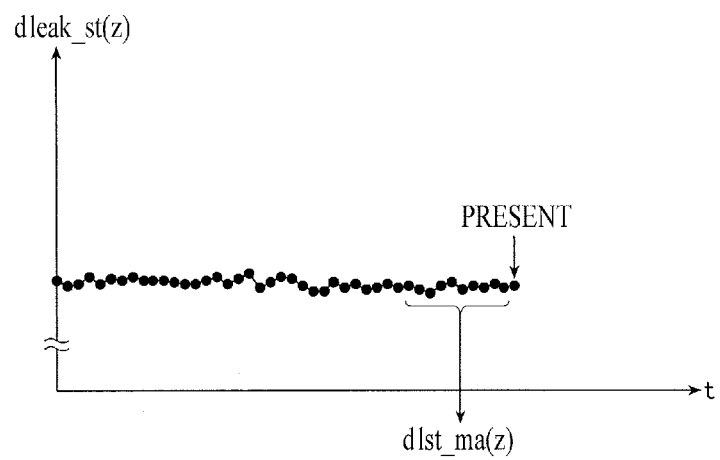
FIG. 12 is a diagram describing a method to calculate moving average.

For example, as shown in FIG. 12, an average of the statistic value dleak_st(z) of the leak data dleak for each readout IC 16 (in other words, moving average dlst_ma(z)) is calculated for each readout processing. The statistic values dleak_st(z) of the average are the values calculated for each readout processing of a predetermined number of processing (for example, 10 times of processing) in the past including the readout processing directly before the present readout processing. In this case, known methods such as simple moving average, weighted moving average, exponential moving average, etc. can be used as the calculating method of the moving average dlst_ma(z). Then, according to the formula below, the difference Δd(z) between the statistic value dleak_st(z) of the leak data dleak calculated in the present readout processing and the moving average dlst_ma(z) calculated as described above is calculated for each readout IC 16, $$\Delta d(z) = d\text{leak\_st}(z) - d\text{lst\_ma}(z) \quad (1)$$

It is possible to configure the control unit 22 to calculate the above difference Δd(z) for each readout IC 16, to extract the maximum value Δdmax from the calculated difference Δd(z), and to judge whether the maximum value Δdmax of the difference Δd(z) is equal to or more than a threshold Δdth. The method of detecting the start of irradiation of radiation based on this detecting method 2α is hereinafter referred to as a difference method.

Figure 13:
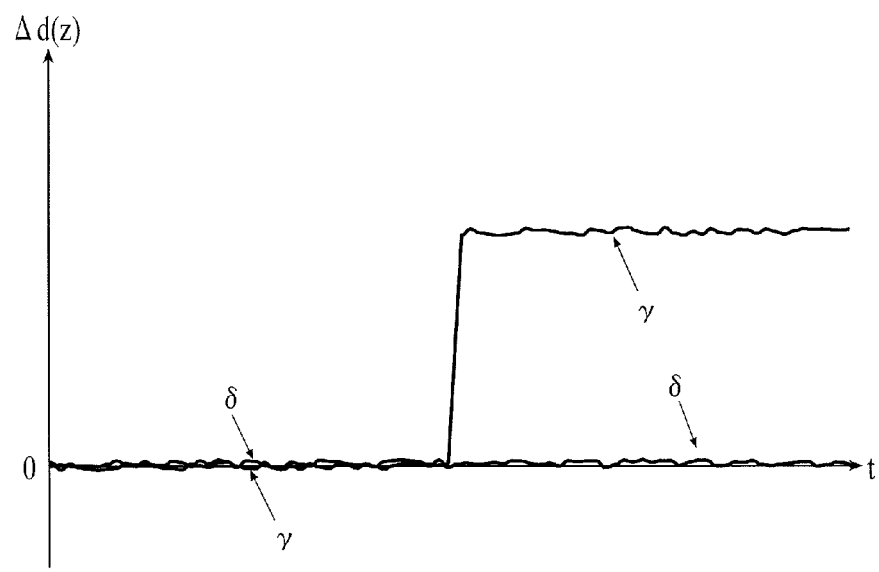
FIG. 13 is a graph showing an example of development through time of each difference calculated for each readout IC.
Figure 14:
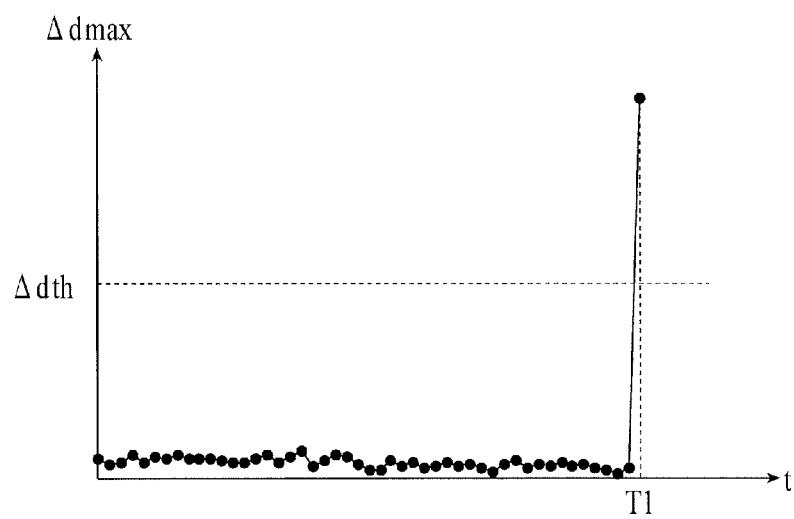
FIG. 14 is a graph showing an example of development through time of a maximum value of the calculated difference.
Figure 15:
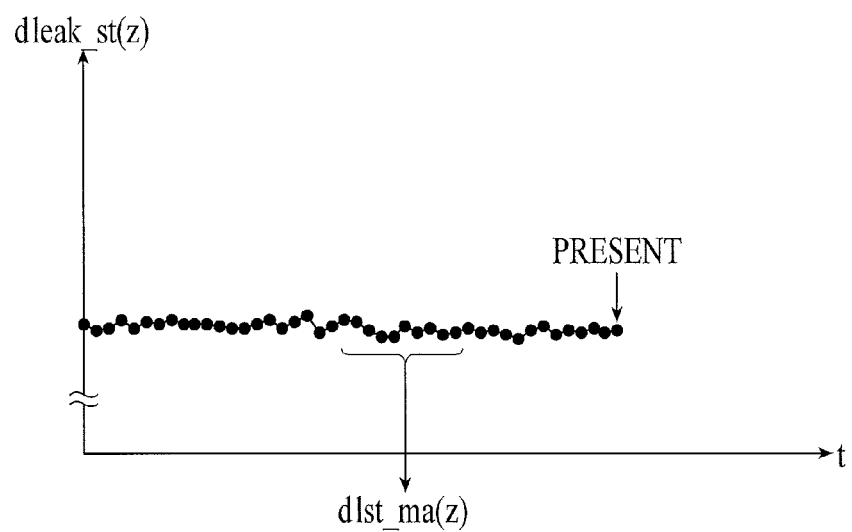
FIG. 15 is a diagram describing a method to calculate moving average which is a method different from the method shown in FIG. 12.

According to the above, the difference Δd(z) between the statistic value dleak_st(z) of the leak data dleak and the moving average dlst_ma(z) is calculated, and the variation of each readout IC 16 due to readout attributes is balanced. As shown in FIG. 13, when the radiation is not irradiated to the radiation image capturing apparatus 1, the calculated value of the difference Δd(z) becomes almost 0 in any of the readout IC 16 and the difference Δd(z) also becomes almost 0. When the irradiation of the radiation starts, there is at least a readout IC 16 where the statistic value dleak_st(z) based on the leak data dleak read out in the present readout processing becomes drastically larger than the moving average dst_ma(z), and as shown in FIG. 14, the maximum value Δdmax of the difference Δd(z) surely becomes equal to or larger than the threshold value Δdth (see time T1 in FIG. 14). Therefore, it is possible to accurately detect that the irradiation of radiation started. As shown in FIG. 15, it is possible to calculate the moving average dlst_ma(x) of the statistic value dleak_st(z) of the leak data dleak for each readout IC 16 calculated in each readout processing for a predetermined number of processing (for example, 10 times of processing) in the past including the readout processing a predetermined number of processing before (for example, 10, 50, etc. times of processing) from the present readout processing of leak data dleak.

[Detecting Method 2β (Integrating Method)]

Alternatively, for example, a time integrated value ΣΔd (also referred to as integral value) of the difference Δd(z) between the statistic value dleak_st(z) of the leak data dleak and the moving average dlst_ma(z) can be calculated for each readout IC 16, and it is possible to judge whether there is a readout IC 16 with the integrated value ΣΔd equal to or larger than the threshold value ΣΔdth. The method of detecting start of irradiation of radiation based on the detecting method 2β is hereinafter referred to as the integrating method.

Although illustration is not shown, in such configuration, when the radiation is not irradiated to the radiation image capturing apparatus 1, the statistic value dleak_st(z) of the leak data dleak is varied and becomes larger or smaller than the moving average dlst_ma(z). Therefore, the integrated value ΣΔd of the difference Δd(z) changes at a value close to 0.

However, when the irradiation of radiation to the radiation image capturing apparatus 1 starts, even if the radiation amount rate of the radiation irradiated from the radiation generating apparatus 55 to the radiation image capturing apparatus 1 is very small, the statistic value dleak_st(z) of the leak data dleak becomes a value significantly larger than the moving average dlst_ma(z), and the difference Δd(z) of the above mostly becomes a positive value. Therefore, according to the above configuration, when the irradiation of radiation to the radiation image capturing apparatus 1 starts, the integrated value ΣΔd increases, and becomes a value equal to or more than the threshold ΣΔdth. Therefore, even if the amount of radiation irradiated from the radiation generating apparatus 55 to the radiation image capturing apparatus 1 is very small, the start of irradiation of radiation to the radiation image capturing apparatus 1 can be accurately detected.

[Characteristic Configuration of the Present Invention]

Next, the characteristic configuration of the present invention in the radiation image capturing system 50 is described. Moreover, the operation of the radiation image capturing system 50 and the radiation image capturing apparatus 1 of the present embodiment is also described.

As described above, according to the present embodiment, the detecting unit 22 (control unit 22 of the present embodiment) of the radiation image capturing apparatus 1 can use the above mentioned [first detecting method] and is able to detect the start of irradiation of radiation based on the value output from the radiation sensor 25 (see FIG. 1, FIG. 2, FIG. 4). As described above, the detecting unit 22 can use the above described [second detecting method] such as detecting method A, B, 2α (difference method), 2β, (integrating method), and is able to detect the start of irradiation of radiation based on the value such as leak data dleak, etc. read out by the readout circuit 17.

It is well known that typically, the consumption amount of electric power of the radiation sensor 25 is small. As described above, at present, usually most readout circuits 17 consume a relatively large amount of electric power when readout is performed. Therefore, comparing the above two detecting methods, the consumption amount of electric power is smaller in the [first detecting method] which uses the output value from the radiation sensor 25 without readout of the readout circuit 17 than the [second detecting method] which uses the leak data dleak, etc. read out by each readout circuit 17.

When the [second detecting method] is employed and the start of radiation of irradiation is detected based on the read out leak data dleak, etc., even under the condition of capturing by irradiating radiation to the radiation image capturing apparatus 1 narrowed to the irradiating field as shown in FIG. 10, by using the detecting method 2α (difference method) as described above with reference to FIG. 11 to FIG. 14, the start of irradiation of radiation can be accurately detected. In addition to when the irradiating field of the radiation is narrowed to the center portion of the radiation entrance face R of the radiation image capturing apparatus 1 as shown in FIG. 10, although illustration is omitted, it is clear from the above description that by using the detecting method 2α (difference method), it is possible to accurately detect the start of irradiation of radiation when the irradiating field of the radiation is narrowed to the edge portion of the radiation entrance face R of the radiation image capturing apparatus 1, for example. As described above, when the [second detecting method] is employed, the detecting unit 22 of the radiation image capturing apparatus 1 is able to accurately detect the start of irradiation of radiation under any capturing condition.

For example, under capturing conditions such as, the subject is an infant or the capturing is Schuller capturing of a hearing organ, the radiation irradiated from the radiation generating apparatus 55 may be weak, in other words, the radiation amount rate (in other words, the amount of radiation for a unit of time) may be small. However, according to the above described [second detecting method], by using the detecting method 2β, (integrating method), the detecting unit 22 of the radiation image capturing apparatus 1 is able to accurately detect the irradiation of radiation.

On the other hand, in the [first detecting method] using the radiation sensor 25, under the capturing condition of narrowing the irradiating field of the radiation as described above, when the radiation with the narrowed irradiating field is irradiated in a position where the radiation sensor 25 is provided, it is possible to detect the start of irradiation of radiation. However, when the radiation is irradiated in a position other than the position where the radiation sensor 25 is provided, it is not possible to detect the start of irradiation of radiation. Moreover, as described above, when weak radiation is irradiated from the radiation generating apparatus 55, even if the signal output from the radiation sensor 25 due to the irradiation of radiation rises, the range of the rise is small. Therefore, the signal does not become equal to or larger than a set threshold value and the start of irradiation of radiation cannot be detected. Therefore, when the [first detecting method] is employed, the capturing condition that the detecting unit 22 of the radiation image capturing apparatus 1 can accurately detect the start of irradiation of radiation is limited.

As described above, according to the present embodiment, the detecting unit 22 of the radiation image capturing apparatus 1 uses either one of the following two methods to detect the start of irradiation of radiation, the [first detecting method] which uses the radiation sensor 25 and where although the consumption amount of electric power is small, the capturing condition that the start of irradiation of radiation can be detected is limited, or the [second detecting method] which uses the readout circuit 17 to read out leak data dleak, etc., and where although the consumption amount of electric power is large, the start of irradiation of radiation can be detected under any capturing condition.

The [first detecting method] of the present invention is not limited to using the radiation sensor 25 as in the present embodiment, and any detecting method can be employed as the [first detecting method] if the detecting method is a method where although the consumption amount of electric power is small, the capturing condition that the start of irradiation of irradiation can be detected is limited. The [second detecting method] of the present invention is not limited to using the leak data dleak, etc. read out by the readout circuit 17 as described in the present embodiment, and any detecting method can be employed as the [second detecting method] if the detecting method is a method where although the consumption amount of electric power is large, the start of irradiation of radiation can be detected under any capturing condition.

Although illustration is omitted, as the [first detecting method] other than the present embodiment, it is possible to employ the detecting method as described in Japanese Patent Application Laid-Open Publication No. 2009-219538, where an electric current detecting unit which detects an electric current which passes through the bias line 9 and the connecting line 10 (see FIG. 4, etc.) can be employed. In this case, since the electric current which passes the bias line 9, etc. increases when the radiation is irradiated, the start of irradiation of radiation can be detected when the value of the detected electric current is equal to or more than, for example, a set threshold value. For example, in this case, when the radiation amount rate of the radiation irradiated to the radiation image capturing apparatus 1 is small, the range of rise of the electric current which passes the bias line 9 becomes small, the value of the detected electric current does not become equal to or more than a threshold value, and it may not be possible to detect the start of irradiation of radiation. Therefore, in this case also there is a possibility that the capturing condition that the start of irradiation of radiation can be accurately detected is limited. In this case, the consumption amount of electric power by the electric current detecting unit is to be smaller than the consumption amount of electric power in the [second detecting method] using the readout circuit 17, for example.

As the [second detecting method] other than the present embodiment, for example, the method as described in Japanese Patent Application Laid-Open Publication No. 2011-172606 can be employed, where the scanning driving unit 15 and the readout circuit 17 (see FIG. 4, etc.) is operated from before the start of irradiation of radiation to perform the readout processing of the image data, the readout processing of image data is performed continuously after the start of irradiation of radiation, and after the end of the irradiation of radiation, the image data D as the main image can be obtained by adding the image data read out for each frame. In such case, the consumption amount of electric power becomes large because the readout operation is performed in each readout circuit 17. However, in this case, similar to the [detecting method 2B] of the [second detecting method] of the present embodiment, since the value of the read out image data increases after the irradiation of radiation starts, for example, the start of irradiation of radiation can be detected when the image data becomes equal to or more than a threshold value. Then, the read out image data is stored in the storage unit 23 (see FIG. 4, etc.) for each frame, and by applying the detecting method 2α (difference method) and the detecting method 2β, (integrating method) on the image data similar to the above, the irradiation of radiation can be accurately detected even if the irradiating field of the radiation irradiated to the radiation image capturing apparatus 1 is narrowed or the radiation amount rate of the irradiated radiation is small.

According to the present embodiment, as described above, the detecting unit 22 of the radiation image capturing apparatus 1 is able to use either one of the following two methods to detect the start of irradiation of radiation, the [first detecting method] where although the consumption amount of electric power is small, the capturing condition that the start of irradiation of radiation can be detected is limited, or the [second detecting method] where although the consumption amount of electric power is large, the start of irradiation of radiation can be detected under any capturing condition.

According to the present embodiment, the detecting unit 22 of the radiation image capturing apparatus 1 selects whether to detect the start of irradiation of radiation using either the [first detecting method] or the [second detecting method] based on the capturing condition transmitted from the console 58 (see FIG. 5 or FIG. 6). Then, the detecting unit 22 performs the processing of detecting start of irradiation of radiation using the selected detecting method. Instead of transmitting the capturing condition from the console 58 to the radiation image capturing apparatus 1, the console 58 may select either the [first detecting method] or the [second detecting method] based on the capturing condition and transmit the information of the selected detecting method to the radiation image capturing apparatus 1 from the console 58. Then, the detecting unit 22 of the radiation image capturing apparatus 1 can use the detecting method transmitted from the console 58 to perform the processing of detecting the start of irradiation of radiation.

The easiest method for the console 58 to obtain the capturing condition is, the operator such as the radiation technologist inputting the capturing condition in the console 58 for each capturing, and this method can be employed in the present invention. However, according to the present embodiment, the radiation image capturing is performed based on capturing order information, and this embodiment is described below.

For example, as shown in FIG. 16, the following information is specified as the capturing condition in the capturing order information, the information including patient information such as "patient ID" P2, "patient name" P3, "sex" P4, "age" P5, and "diagnosis department" P6, and capturing information such as "capturing site" P7, "capturing direction" P8, and "bucky ID" P9 of the bucky to be used, and the like. According to the example of FIG. 16, bucky ID "001" and "002" each respectively represent standing position capturing bucky apparatus 51A and recumbent position capturing bucky apparatus 51B, and bucky ID "003" represents using the FPD independently without mounting the bucky apparatus 51. The "bucky ID" P9 of the bucky apparatus to be used does not have to be specified in the capturing order information. According to the present embodiment, the "capturing order ID" P1 is automatically assigned to each piece of capturing order information in the order the capturing order is registered.

According to the present embodiment, the operator such as the radiation technologist operates the console 58, and the console 58 is able to obtain capturing order information from HIS (Hospital Information System) and RIS (Radiology Information System) not shown through the network not shown. The method of input of capturing order information to the console 58 is suitably determined, and the console can obtain the capturing order information from the RIS etc., as described above, or alternatively, the capturing order information can be input to the console 58 by, for example, inputting with a barcode, inputting manually by the operator, or the like.

According to the present embodiment, when the console 58 obtains the capturing order information, the console 58 displays a list of each piece of obtained capturing order information on the selection screen H1 displayed on the display unit 58a. The selection screen H1 may be configured as shown in FIG. 17. In other words, a capturing order information display field h11 to display a list of the capturing order information, and a selection button h12 to select the capturing order information of the scheduled capturing, are provided corresponding to each piece of capturing order information on the selection screen H1. On the side below the capturing order information display field h11, it is possible to display an enter button h13 and a return button h14.

The operator such as the radiation technologist clicks the selection button h12 and is able to select the capturing order information corresponding to the radiation image capturing to be performed. According to the present embodiment, when the capturing order information is selected, the console 58 extracts the necessary capturing condition from the selected capturing order information to transmit the capturing condition to the radiation image capturing apparatus 1. In the embodiment described below, the detecting unit 22 of the radiation image capturing apparatus 1 selects either one of the [first detecting method] or the [second detecting method] based on the capturing condition transmitted from the console 58. The description similarly applies when the console 58 selects either the [first detecting method] or the [second detecting method] based on the capturing condition extracted from the capturing order information and transmits the information of the selected detecting method to the radiation image capturing apparatus 1, and therefore the description for such configuration is omitted.

Specifically, for example, when the capturing order information is selected as described above, the console 58 transmits the necessary capturing condition such as "capturing site" P7, "age" P5 in the selected capturing order information to the radiation image capturing apparatus 1. Alternatively, the capturing order information itself may be transmitted.

For example, the detecting unit 22 of the radiation image capturing apparatus 1 includes in advance a table of the capturing conditions where it is necessary to select the [second detecting method]. As the capturing condition where the [second detecting method] needs to be selected, there are, for example, capturing conditions specifying, "hand", "arm portion", "leg portion", etc. as the "capturing site" P7. When the "hand", "arm portion", "leg portion", etc. are specified as the "capturing site", the radiation irradiated from the radiation generating apparatus 55 may be irradiated with the irradiating field narrowed, and therefore, the [second detecting method] should be employed in order to detect the start of irradiation of radiation accurately. As described here, according to the present embodiment, the capturing condition where the [second detecting method] should be applied includes the capturing condition where there is a possibility that the radiation may be irradiated to the radiation image capturing apparatus with a narrowed irradiating field.

For example, the capturing condition of specifying "Schuller capturing for a hearing organ", etc. as the "capturing site" P7 or the capturing condition specifying an age of an infant as the "age" P5 are capturing conditions where the [second detecting method] needs to be selected. According to such capturing conditions, the radiation may be irradiated from the radiation generating apparatus 55 to the subject or the radiation image capturing apparatus 1 with a small radiation amount rate, and therefore, the [second detecting method] should be employed in order to detect the start of irradiation of radiation accurately. As described here, according to the present embodiment, the capturing condition where the [second detecting method] should be applied includes the capturing condition where there is a possibility that the radiation amount rate of the radiation irradiated to the radiation image capturing apparatus 1 may be too small so that the start of irradiation of radiation cannot be detected by using the [first detecting method].

Then, when the capturing order information or the capturing condition is transmitted from the console 58, the detecting unit 22 of the radiation image capturing apparatus 1 extracts the capturing condition when the capturing order information is transmitted, and searches whether the extracted or transmitted capturing condition matches with the capturing condition described in the above table. When the capturing condition matches with the capturing condition described in the table, the detecting unit 22 selects detecting start of irradiation of radiation using the [second detecting method], and performs processing of detecting start of irradiation of radiation using the selected [second detecting method].

When the capturing condition does not match with the capturing condition described on the table, the detecting unit 22 of the radiation image capturing apparatus 1 selects detecting the start of irradiation of radiation using the [first detecting method], and performs processing of detecting start of irradiation of radiation using the selected [first detecting method]. Alternatively, opposite of the present embodiment, it is possible to include in advance a table of the capturing conditions where the detecting unit 22 of the radiation image capturing apparatus 1 needs to select the [first detecting method]. In this case, the table lists the capturing conditions where the start of irradiation of radiation can be surely detected using the [first detecting method] using the radiation sensor 25, etc.

As described above, according to the radiation image capturing system 50 and the radiation image capturing apparatus 1 of the present embodiment, the detecting unit 22 of the radiation image capturing apparatus 1 detects the start of irradiation of radiation using either the [first detecting method] where the consumption amount of electric power is small but the capturing condition that the start of irradiation of radiation can be detected is limited or the [second detecting method] where the consumption amount of electric power is large but the start of irradiation of radiation can be detected under any capturing condition.

Then, when the console 58 obtains the capturing condition by obtaining the capturing order information, etc., the console 58 transmits the obtained capturing condition (including when the capturing order information itself is obtained) to the radiation image capturing apparatus 1 and the detecting unit 22 of the radiation image capturing apparatus 1 selects whether to detect the start of irradiation of radiation using either the [first detecting method] or the [second detecting method] based on the capturing condition. Alternatively, the console 58 selects whether to detect the start of irradiation of radiation using either the [first detecting method] or the [second detecting method] based on the capturing condition, and transmits the information of the selected detecting method to the detecting unit 22 of the radiation image capturing apparatus 1. Then, the detecting unit 22 of the radiation image capturing apparatus 1 uses the selected detecting method to perform processing of detecting start of irradiation of radiation.

Therefore, when the capturing condition of the radiation image capturing to be performed includes capturing conditions where it is possible to detect the start of irradiation of radiation using the [first detecting method], the detecting unit 22 of the radiation image capturing apparatus 1 or the console 58 selects the [first detecting method]. Therefore, the detecting unit 22 of the radiation capturing apparatus 1 is able to detect the start of irradiation of radiation accurately using the [first detecting method]. The [first detecting method] is reliably selected when the start of irradiation of radiation can be accurately detected by using the [first detecting method] with a small consumption amount of electric power. Therefore, the [second detecting method] which consumes a large amount of electric power is not selected. Therefore, the start of irradiation of radiation can be detected in a state where the consumption amount of electric power is saved in the processing of detecting the start of irradiation of radiation.

When the capturing condition of the radiation image capturing to be performed includes a capturing condition where there is a possibility that the start of irradiation of radiation cannot be detected by using the [first detecting method], the [second detecting method] is selected. Therefore, with such capturing condition, the detecting unit 22 of the radiation image capturing apparatus 1 is able to accurately detect the start of irradiation of radiation using the [second detecting method] that is able to detect the start of irradiation of radiation under any capturing condition.

According to the radiation image capturing system 50 or the radiation image capturing apparatus 1 of the present embodiment, it is possible to accurately detect the start of irradiation of radiation under any capturing condition and to accurately perform radiation image capturing while saving the consumption amount of electric power in the processing of detecting the start of irradiation of radiation as much as possible.

The present invention is not limited to the above embodiments and modifications, and the present invention can be suitably modified without leaving the scope of the present invention.

The entire disclosure of Japanese Patent Application No. 2013-110471 filed on May 27, 2013 including description, claims, drawings, and abstract are incorporated herein by reference in its entirety.

What is claimed is:

1. A radiation image capturing system comprising:
   a radiation image capturing apparatus including,
   a plurality of scanning lines and a plurality of signal lines;
   a plurality of radiation detecting elements arranged two-dimensionally;
   a scanning driving unit which switches voltage applied to each scanning line between on voltage and off voltage;
   a switch element which is connected to each scanning line, wherein electric charge is accumulated in the radiation detecting element when the off voltage is applied, and the electric charge accumulated in the radiation detecting element is discharged to the signal line when the on voltage is applied;

a readout circuit which reads out the electric charge discharged from the radiation detecting element as image data;

a detecting unit which detects start of irradiation of radiation using either a first detecting method or a second detecting method, the first detecting method wherein consumption amount of electric power is small but a capturing condition with which the start of irradiation of radiation can be detected is limited, and the second detecting method wherein consumption amount of electric power is large but the start of irradiation of radiation can be detected under any capturing condition; and a communication unit which communicates with an external device; and a console including a communication unit to communicate with the radiation image capturing apparatus to be able to obtain the capturing condition, wherein, when the console obtains the capturing condition, the console transmits the obtained capturing condition to the radiation image capturing apparatus; and the detecting unit of the radiation image capturing apparatus selects whether to detect the start of irradiation of radiation using either the first detecting method or the second detecting method based on the capturing condition transmitted from the console, and performs processing of detecting the start of irradiation of radiation using the selected detecting method.

2. The radiation image capturing system of claim 1, wherein, instead of transmitting the obtained capturing condition to the radiation image capturing apparatus, the console selects either of the first detecting method or the second detecting method based on the obtained capturing condition, and transmits information of the selected detecting method to the radiation image capturing apparatus; and the detecting unit of the radiation image capturing apparatus performs processing of detecting the start of irradiation of radiation using the detecting method transmitted from the console.

3. The radiation image capturing system of claim 1, wherein, according to the second detecting method, the detecting unit detects the start of irradiation of radiation based on leak data where the readout circuit reads out the electric charge leaked from each radiation detecting element through each switch element in a state where the off voltage is applied to each scanning line from the scanning driving unit of the radiation image capturing apparatus to set each switch element to an off state, or based on a value calculated from the leak data.

4. The radiation image capturing system of claim 1, wherein, according to the second detecting method, the detecting unit detects the start of irradiation of radiation based on data for detecting the start of irradiation read out with the readout circuit when the on voltage is sequentially applied to each scanning line from the scanning driving unit of the radiation image capturing apparatus, or based on a value calculated from the data for detecting the start of irradiation.

5. The radiation image capturing system of claim 1, wherein, the capturing condition where the second detecting method is applied includes a capturing condition with a possibility that the radiation is irradiated to the radiation image capturing apparatus with an irradiating field narrowed.

6. The radiation image capturing system of claim 1, wherein, the capturing condition where the second detecting method is applied includes a capturing condition with a possibility that a radiation amount rate of the radiation irradiated to the radiation image capturing apparatus is too small so that the start of irradiation of radiation cannot be detected using the first detecting method.

7. The radiation image capturing system of claim 1, wherein, the radiation image capturing apparatus is a portable type including a battery.

8. The radiation image capturing system of claim 1, wherein, the console is able to obtain capturing order information specifying the capturing condition; and when the console obtains the capturing order information, the console (i) transmits the obtained capturing order information or the capturing condition extracted from the capturing order information to the radiation image capturing apparatus, or (ii) selects either of the first detecting method or the second detecting method based on the capturing condition extracted from the obtained capturing order information and transmits information of the selected detecting method to the radiation image capturing apparatus.

9. A radiation image capturing apparatus comprising:

a plurality of scanning lines and a plurality of signal lines;

a plurality of radiation detecting elements arranged two-dimensionally;

a scanning driving unit which switches voltage applied to each scanning line between on voltage and off voltage;

a switch element which is connected to each scanning line, wherein electric charge is accumulated in the radiation detecting element when the off voltage is applied, and the electric charge accumulated in the radiation detecting element is discharged to the signal line when the on voltage is applied;

a readout circuit which reads out the electric charge discharged from the radiation detecting element as image data; and a detecting unit which detects start of irradiation of radiation using either a first detecting method or a second detecting method, the first detecting method wherein consumption amount of electric power is small but a capturing condition with which the start of irradiation of radiation can be detected is limited, and the second detecting method wherein consumption amount of electric power is large but the start of irradiation of radiation can be detected under any capturing condition, wherein, the detecting unit selects whether to detect the start of irradiation of radiation using either the first detecting method or the second detecting method based on a specified capturing condition, and performs processing of detecting the start of irradiation of radiation using the selected detecting method.

* * * * *